US006645431B2

(12) United States Patent
Astle

(10) Patent No.: US 6,645,431 B2
(45) Date of Patent: Nov. 11, 2003

(54) APPARATUS FOR AUTOMATED MAGNETIC SEPARATION OF MATERIALS IN LABORATORY TRAYS

(76) Inventor: Thomas W. Astle, 607 Harborview Rd., Orange, CT (US) 06477

( * ) Notice: Subject to any disclaimer, the term of this patent is extended or adjusted under 35 U.S.C. 154(b) by 359 days.

(21) Appl. No.: 09/766,816

(22) Filed: Jan. 22, 2001

(65) Prior Publication Data

US 2002/0098121 A1 Jul. 25, 2002

(51) Int. Cl.$^7$ ............... B01L 3/00; B01L 9/00; G01N 33/553; C12N 13/00; B01D 35/06; B01D 25/32
(52) U.S. Cl. ............ 422/99; 422/102; 422/104; 436/526; 435/173.1; 210/695; 210/222; 210/232
(58) Field of Search ............ 422/99, 100, 102, 422/104; 210/695, 222, 232; 435/173.1; 436/523, 526

(56) References Cited

U.S. PATENT DOCUMENTS

| 5,558,839 | A | * | 9/1996 | Matte et al. ............ 422/101 |
|---|---|---|---|---|
| 5,674,741 | A | * | 10/1997 | Watanabe et al. ......... 435/283.1 |
| 5,779,907 | A | | 7/1998 | Yu |
| 6,074,609 | A | * | 6/2000 | Gavin et al. ............ 422/99 |
| 6,148,878 | A | * | 11/2000 | Ganz et al. ............ 141/129 |
| 6,325,114 | B1 | * | 12/2001 | Bevirt et al. ............ 141/130 |
| 6,333,008 | B1 | * | 12/2001 | Leistner et al. ............ 422/64 |
| 6,368,561 | B1 | * | 4/2002 | Rutishauser et al. ........ 422/99 |
| 6,379,625 | B1 | * | 4/2002 | Zuk, Jr. ............ 422/101 |
| 6,406,670 | B1 | * | 6/2002 | Earley et al. ............ 422/99 |
| 6,485,690 | B1 | * | 11/2002 | Pfost et al. ............ 422/102 |
| 2002/0070173 | A1 | * | 6/2002 | Otto et al. ............ 210/695 |
| 2002/0094581 | A1 | * | 7/2002 | Cole ............ 436/174 |
| 2003/0038071 | A1 | * | 2/2003 | Hansen et al. ............ 210/222 |

* cited by examiner

Primary Examiner—Jill Warden
Assistant Examiner—Brian R Gordon
(74) Attorney, Agent, or Firm—John H. Crozier

(57) ABSTRACT

In a preferred embodiment, an apparatus for automated magnetic separation of materials in laboratory trays, including: a frame upon an upper surface of which a multiwell laboratory tray may be placed; a base plate on which is mounted a plurality of upstanding magnets disposed below the upper surface; and apparatus to raise the base plate such as to insert the upstanding magnets into interwell spaces in the laboratory tray.

7 Claims, 4 Drawing Sheets

APPARATUS FOR AUTOMATED MAGNETIC SEPARATION OF MATERIALS IN LABORATORY TRAYS

BACKGROUND OF THE INVENTION

1. Field of the Invention

The present invention relates to magnetic separation generally and, more particularly, but not by way of limitation, to a novel apparatus that permits the automatic separation of magnetic components in a laboratory microplate.

2. Background Art

In the field of biology, there are requirements for the separation of one constituent from another. Some of e more commonly used methods are centrifugation, filtration, and magnetic separation. Centrifugation uses centrifugal force to provide separation by elements of mass. Filtration on provides separation by size. Magnetic separation uses a magnetic field to attract and hold magnetic particles, or magnetic beads, so that the supernate in which the suspended material is disposed can be removed.

Magnetic beads are particularly useful in immunoassays. Constituents of interest may be coated on the surface of paramagnetic particles. Using an applied magnetic field, the beads may be congregated and retained from the surrounding liquid reagents of reactants. U.S. Pat. No. 5,779,907, issued Jul. 14, 1998, to Yu, and titled MAGENTIC MICROPLATE SEPARATOR, describes a means and method of providing magnetic separation. As described in the patent, a laboratory tray, or microplate, containing a number of vertical wells is placed on a fixture having a number of upstanding cylindrical magnets. The arrangement of wells and magnets is such that each magnet is disposed adjacent four of the wells. Thus, a 96-well plate requires a fixture that has 24 magnets. The magnetic components in the wells are attracted to the sides of the wells adjacent the magnets. The supernate in the wells can then be removed. The apparatus described by Yu is entirely satisfactory for manual use; however, it does not meet the need of processing the large numbers of samples that are required in the fields of genomic and drug discovery research. Automation is required for processing large numbers of samples.

Conventionally, in automated magnetic separation systems, a robotic arm moves the laboratory trays over a fixed plate of magnets. While this provides an improvement over the manual method, it requires an additional positioning of the laboratory tray.

Accordingly, it is a principal object of the present invention to provide an apparatus for magnetic separation that does not require a separate step of positioning of the laboratory plate.

It is a further object of the invention to provide such an apparatus that can be remotely and automatically controlled.

It is an additional object of the invention to provide such an apparatus that can be economically constructed using conventional techniques.

It is another object of the invention to provide such an apparatus that can be part of a robotic liquid handling system.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, an apparatus for automated magnetic separation of materials in laboratory trays, comprising: a frame upon an upper surface of which a multiwell laboratory tray may be placed, a base plate on which is mounted a plurality of upstanding magnets disposed below said upper surface; and means to raise said base plate such as to insert said upstanding magnets into interwell spaces in said laboratory tray.

BRIEF DESCRIPTION OF THE DRAWING

Understanding of the present invention and the various aspects thereof will be facilitated by reference to the accompanying drawing figures, provided for purposes of illustration only and not intended to define the scope of the invention, on which.

DETAILED DESCRIPTION OF THE PREFERRED EMBODIMENTS

Figure 1:
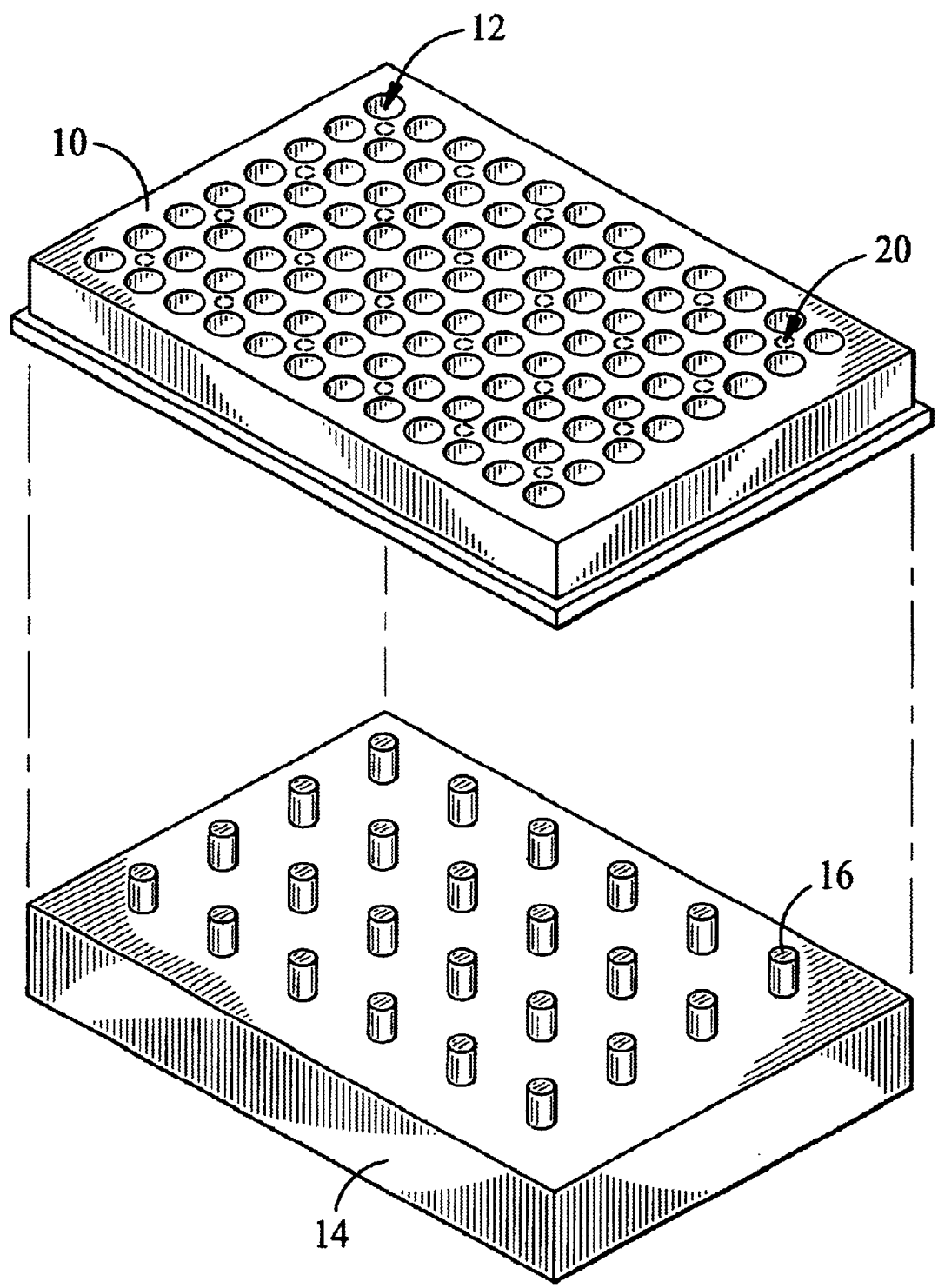
FIG. 1 is an isometric view of a microplate positioned over a plate of magnets.

Reference should now be made to the drawing figures on which similar or identical elements are given consistent identifying numerals throughout the various figures thereof, and on which parenthetical references to figure numbers direct the reader to the view(s) on which the element(s) being described is (are) best seen, although the element(s) may be seen on other figures also.

FIG. 1 illustrates a microplate 10 having a plurality of vertical wells, as at 12, positioned over a plate of magnets 14 having a plurality of upstanding cylindrical magnets, as at 16 Wells 12 and magnets 16 are arranged such that, when microplate 10 and plate of magnets 14 are brought together, each magnet 16 will be moved into one of a plurality of positions, as at 20, in the microplate and, so disposed, each magnet will be adjacent four of the wells. Microplate 10 is shown as having 96 wells arranged in a 8×12 matrix and plate of magnets 14 consequently has 24 magnets. It will be understood, however, that the invention may be applied as well to other numbers of microplate wells. In this position, the magnetic flux surrounding each magnet 16 encompasses four adjacent wells 12. Paramagnetic particles in wells 12 will be attracted by this field and will be drawn to the sidewalls of the wells, adjacent to each magnet 16. The supernate can then be withdrawn from the wells by, for example, aspiration.

Figure 2:
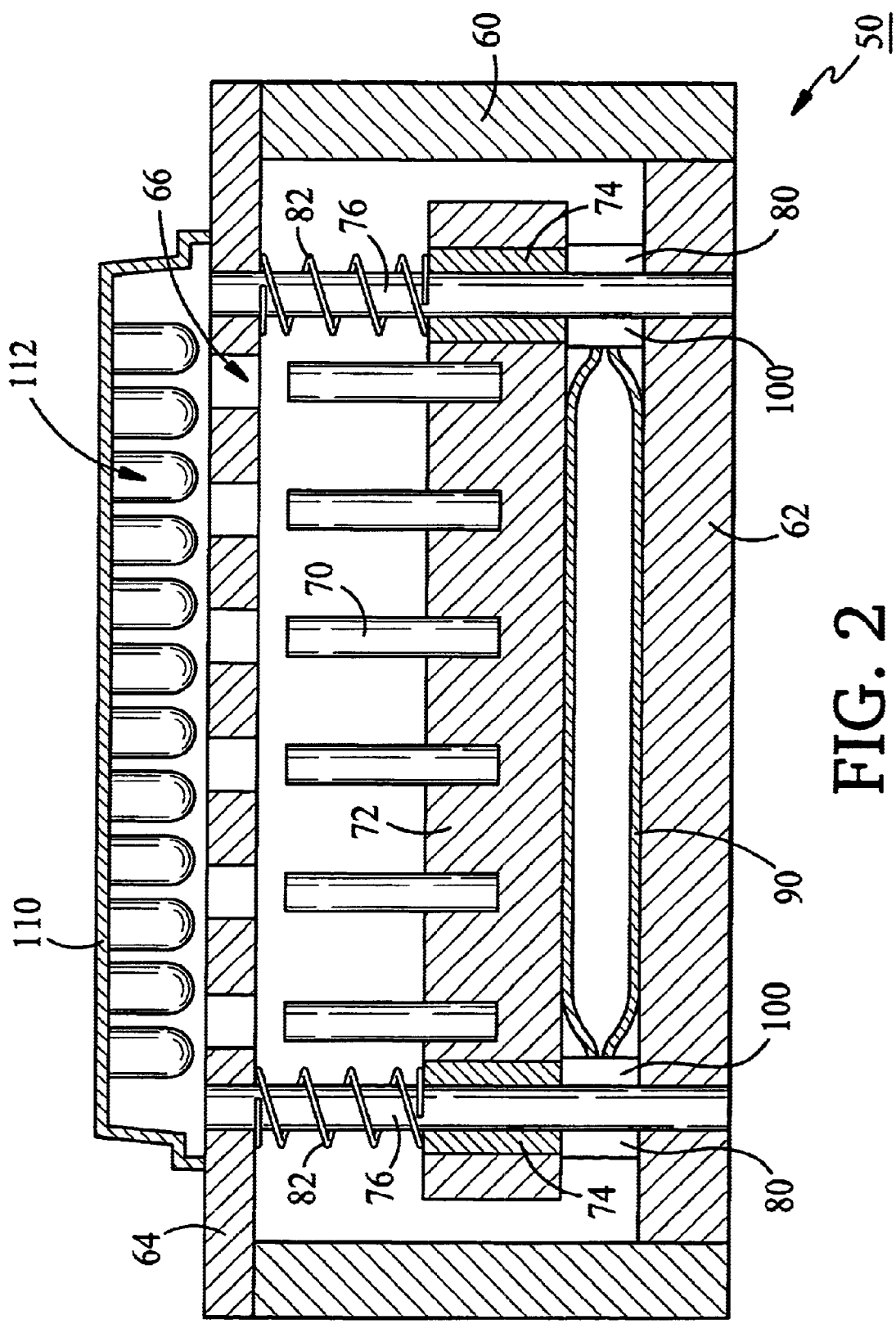
FIG. 2 is a side elevational view of the invention, partially in cross-section, with a plate of magnets in lowered position.

FIG. 2 illustrates an apparatus, constructed according to the present invention, and generally indicated by the reference numeral 50. Apparatus 50 includes a frame 60 having a horizontal bottom plate 62 and a horizontal top plate 64, the latter having a plurality of vertical holes defined therethrough, as at 66. A plurality of upstanding vertical magnets, as at 70, is fixedly attached to a horizontal, non-magnetic base plate 72 that includes four bearings 74 (only two shown) journaled on four vertical guide pins 76 (only two shown) extending between and fixedly attached to bottom plate 62 and top plate 64. Thus arranged, base plate 72 may move vertically upwardly and downwardly in frame 60. Base plate 72 is held in its down position against four stops 80 (only two shown) fixedly attached to bottom plate 62 by the action of four compression springs 82 (only two shown) disposed around guide pins 76 and compressed between the lower surface of top plate 64 and the upper surface of the base plate.

A flexible bladder 90 disposed between the upper surface of bottom plate 62 and the lower surface of base plate 72 provides the motive force to raise the base plate. Bladder 90 may be simply constructed from a bicycle inner tube that is clamped between two clamps 100 fixedly attached to bottom plate 62. One of clamps 100 is fitted with an air line connection (not shown) to permit flow of pressurized air to the closed interior of bladder 90.

As shown on FIG. 2, a microplate 110 having a plurality of vertical wells 112 has been placed on the upper surface of top plate 64. Since base plate 72 is shown in its lowered position, magnets 70 are spaced below wells 112.

Figure 3:
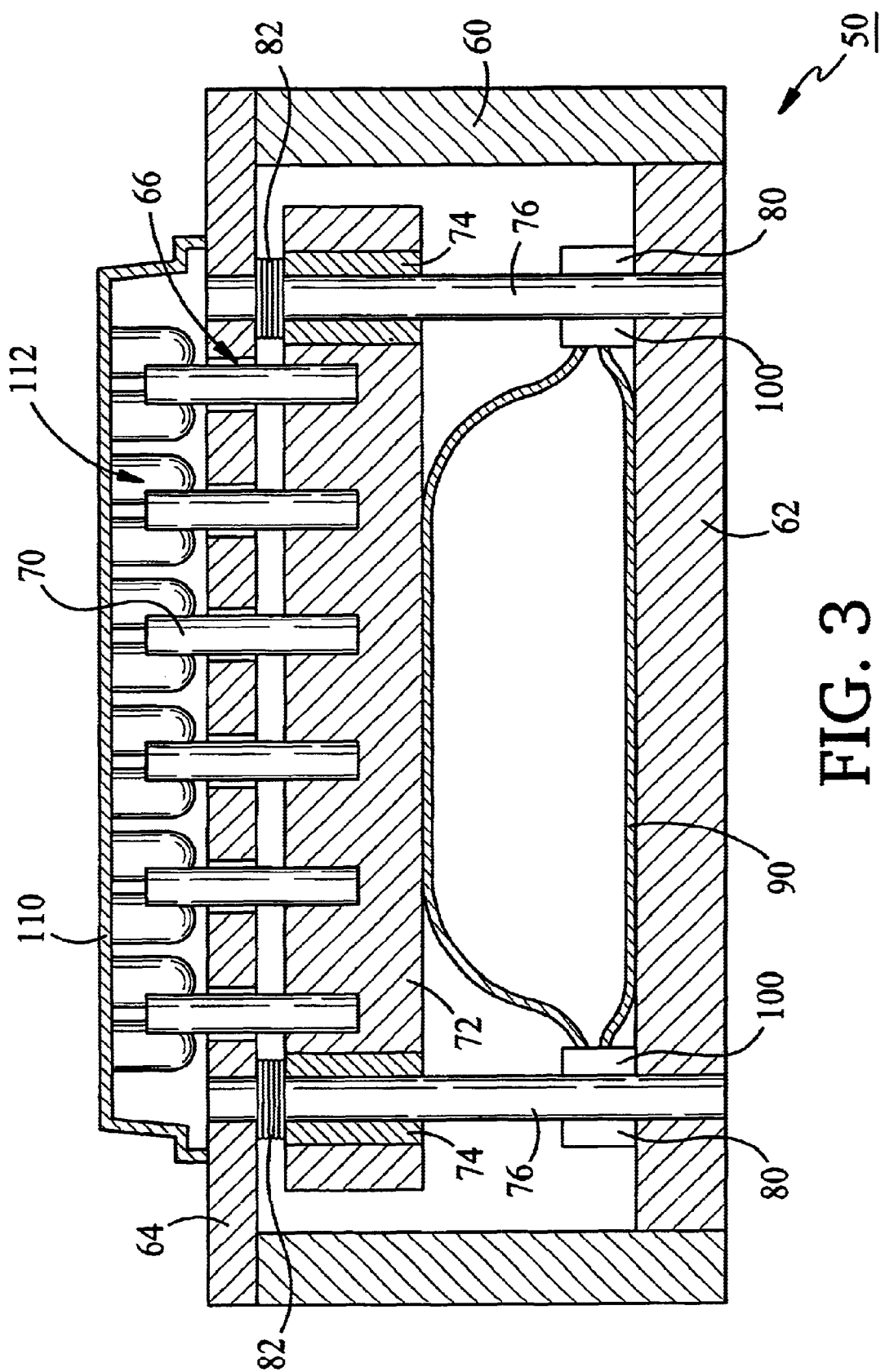
FIG. 3 is a side elevational view of the invention, partially in cross-section, with a plate of magnets in raised position, such that the magnets are disposed between the wells of the microplate.

FIG. 3 illustrates the elements of apparatus 50 described above (FIG. 2), with pressurized air having been introduced into bladder 90. The inflation of bladder 90 causes base plate 72 to rise, that motion causing magnets 70 to extend through openings 66 and between wells 112. As will be understood from inspection of FIG. 1 and the accompanying text, each of magnets 70 will be inserted adjacent four of wells 112 in microplate 110. Supernate can now be removed from wells 112 by any suitable means such as by aspiration of the supernate. Expansion of bladder 90 is limited by the confines of frame 60. The upward force provided by the inflation of bladder 90 exceeds the downward forces being applied by compression springs 82, permitted the elevation of base plate 72. Venting of compressed air from bladder 90 will cause the bladder to collapse and base plate 72 to return to its lowered position (FIG. 2) by means of the downward force provided by compression springs 82.

Figure 4:
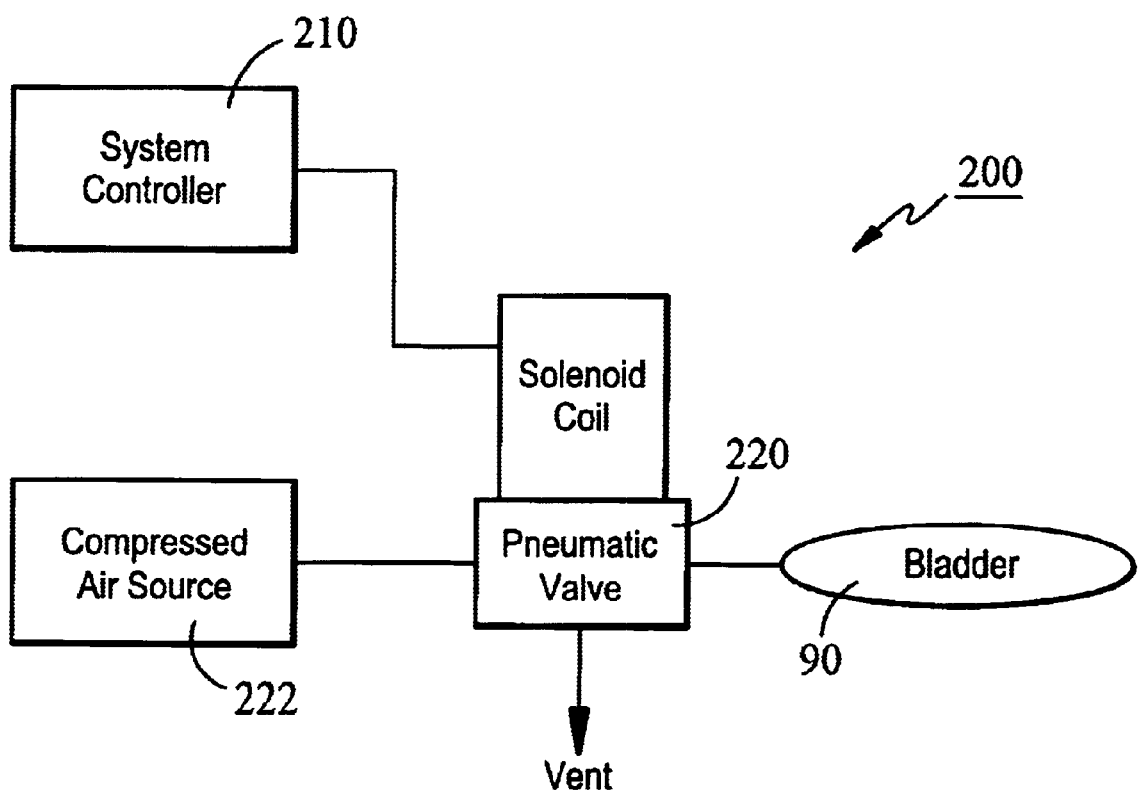
FIG. 4 is a block/schematic view of a control system for the present invention.

FIG. 4 illustrates a control system that may be used with apparatus 50, the control system being generally indicated by the reference numeral 200. Control system 200 includes a system controller 210 that may be a section of a controller used to control other features of a complete analysis system. Controller 210 is operatively connected to control a three-way solenoid valve 220 that permits compressed air from a compressed air source 222 to inflate bladder 90 to raise base plate 72 to its elevated position (FIG. 3) or to vent air from the bladder to cause the base plate to move to its lowered position (FIG. 2).

The present invention provides a simple and effective means of moving magnets into the interwell spacing of a microplate by remote means. In the case described, low air pressure applied to a bladder, lifts the magnets.

Using a remotely controlled method of actuating the magnets into the interwell spacing permits the inclusion of the device into a liquid handling robot. This permits completion automation of the entire liquid handling function. The first step in bioassays, using magnetic beads or particles, is to react the coated elements on the beads with other liquid reagents. This requires the beads to be in suspension to provide full exposure of the reacting elements. Normally, some means of agitation is incorporated, such as shaking or multiple aspirations dispensings.

Following the reaction step is the separation step. A magnetic field is applied, drawing the magnetic beads to the sidewalls of the containing well. This separates the beads from the liquid in the well, permitting the liquid to be withdrawn by an automated pipettor. This process may be repeated multiple times, depending on the assay protocol and how many different reagent reactions are required.

By the use of a remote means of controlling the insertion of the magnets, the action may by easily accommodated in liquid handling robotics control systems, such as supplied by Tomtec, Inc., of Hamden, Conn. An actuating signal is generated in the control system software This signal controls an electrically operated solenoid valve that applies controlled air pressure to the device operating the magnets. By being small and compact, the magnetic device can be located directly on the robot's operating deck. In other words, frame 60 (FIGS. 2 and 3) simply replaces what would have been a fixed nest, to hold the microplate being used for the test.

This simplicity eliminates the necessity of physically moving the microplate from the station where it receives the reagent, without magnetization, to a station with magnetization. The invention permits the system control to apply magnetization on demand where and when it is required.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

The embodiments of the invention in which an exclusive property or privilege is claimed are defined as follows:

1. An apparatus for automated magnetic separation of materials in laboratory trays, comprising:
   (a) a frame upon an upper surface of which a multiwell laboratory tray may be placed;
   (b) a base plate n which is mounted a plurality of upstanding magnets disposed below said upper surface; and
   (c) a flexible bladder to raise said base plate such as to insert said upstanding magnets into interwell spaces in said laboratory tray.

2. An apparatus, as defined in claim 1, wherein: said flexible bladder is supplied with compressed air to provide a motive force.

3. An apparatus, as defined in claim 1, wherein: said flexible bladder is pneumatically operated.

4. An apparatus, as defined in claim 2, wherein: said compressed air is automatically controlled.

5. An apparatus for automated magnetic separation of materials in laboratory trays, comprising:
   (a) a frame upon an upper surface of which a multiwell laboratory tray may be placed;
   (b) a base plate on which is mounted a plurality of upstanding magnets disposed below said upper surface and moveable upwardly and downwardly in said frame, upward movement of said base plate causing insertion of said plurality of upstanding magnets into interwell spaces in said laboratory tray and downward movement of said base plate causing withdrawal of said plurality of upstanding magnets from said interwell spaces; and (c) a flexible bladder to impart said upward movement to said base plate wherein application of compressed air causes said flexible bladder to expand.

6. An apparatus, as defined in claim 5, further comprising: compression springs to assist said downward movement of said base plate when said compressed air is removed from said pneumatically expandable device.

7. An apparatus, as defined in claim 5, wherein: said compressed air is automatically controlled.

* * * * *

UNITED STATES PATENT AND TRADEMARK OFFICE
CERTIFICATE OF CORRECTION

PATENT NO. : 6,645,431 B2
DATED : November 11, 2003
INVENTOR(S) : Thomas W. Astle It is certified that error appears in the above-identified patent and that said Letters Patent is hereby corrected as shown below:

Column 1,
Line 13, "e" is cancelled and -- the -- is inserted therefor.
Line 16, "on" is cancelled and -- only -- is inserted therefor.

Column 4,
Line 48, "n" is cancelled and -- on -- is inserted therefor.

Signed and Sealed this

Thirtieth Day of December, 2003

JAMES E. ROGAN
*Director of the United States Patent and Trademark Office*